(12) United States Patent
Kim

(10) Patent No.: US 11,992,568 B2
(45) Date of Patent: May 28, 2024

(54) STERILIZATION APPARATUS USING PLASMA AND ULTRAVIOLET LIGHT AND STERILIZATION SYSTEM COMPRISING THE SAME

(71) Applicant: Jin Oh Kim, Seoul (KR)

(72) Inventor: Jin Oh Kim, Seoul (KR)

(73) Assignee: Jin Oh Kim, Seoul (KR)

( * ) Notice: Subject to any disclaimer, the term of this patent is extended or adjusted under 35 U.S.C. 154(b) by 33 days.

(21) Appl. No.: 16/978,528

(22) PCT Filed: May 13, 2020

(86) PCT No.: PCT/KR2020/006265
§ 371 (c)(1),
(2) Date: Sep. 4, 2020

(87) PCT Pub. No.: WO2021/049734
PCT Pub. Date: Mar. 18, 2021

(65) Prior Publication Data
US 2023/0100199 A1    Mar. 30, 2023

(30) Foreign Application Priority Data

Sep. 11, 2019  (KR) ........................ 10-2019-0112947

(51) Int. Cl.
*A61L 2/14*    (2006.01)
*A61L 2/10*    (2006.01)
(Continued)

(52) U.S. Cl.
CPC .................................... *A61L 2/14* (2013.01);
*A61L 2/10* (2013.01); *A61L 2/24* (2013.01);
*B64F 1/368* (2013.01); *A61L 2202/23* (2013.01)

(58) Field of Classification Search
CPC ..... A61L 2/14; A61L 2/10; A61L 2/24; A61L 2/208; A61L 2/26; A61L 2202/23;
(Continued)

(56) References Cited

U.S. PATENT DOCUMENTS 9,970,813 B1    5/2018  Gliner et al.
2014/0131595 A1*  5/2014  Nathan ................. A61L 2/0047
                                                 250/504 R
(Continued)

FOREIGN PATENT DOCUMENTS

CN    101920026 A    12/2010
CN    204631271 U    9/2015
(Continued)

OTHER PUBLICATIONS

International Search Report dated Aug. 26, 2020 for International Patent Application No. PCT/KR2020/006265.

*Primary Examiner* — Jason L McCormack
(74) *Attorney, Agent, or Firm* — Baker & McKenzie LLP

(57) ABSTRACT

Disclosed are a sterilization apparatus for sterilizing an object using plasma and ultraviolet light and a sterilization system for an airport including the same. The sterilization apparatus includes a first sterilizer configured to radiate plasma rays toward a sterilization space, a second sterilizer configured to radiate ultraviolet light toward the sterilization space, a sensing unit configured to sense whether an object is placed in the sterilization space, and a controller configured to control an operation of the second sterilizer based on information sensed by the sensing unit.

7 Claims, 8 Drawing Sheets

(51) Int. Cl.
*A61L 2/24* (2006.01)
*B64F 1/36* (2017.01)

(58) Field of Classification Search
CPC ............ A61L 2202/11; A61L 2202/14; A61L 2202/16; B64F 1/368; B64F 1/32; G01N 23/043
USPC .......................................... 250/453.11, 455.11
See application file for complete search history.

(56) References Cited

U.S. PATENT DOCUMENTS

| | | | |
|---|---|---|---|
| 2014/0158910 A1* | 6/2014 | Fletcher | ................... A61L 2/10 250/455.11 |
| 2015/0025300 A1* | 1/2015 | Hill | ........................... A61L 9/22 600/21 |
| 2017/0049915 A1* | 2/2017 | Brais | .................... H05B 47/115 |
| 2019/0262489 A1* | 8/2019 | Yanai | ........................ A61L 2/28 |

FOREIGN PATENT DOCUMENTS

| | | |
|---|---|---|
| CN | 112089860 A | 12/2020 |
| CN | 112168987 A | 1/2021 |
| CN | 113264340 A | 8/2021 |
| CN | 213884322 U | 8/2021 |
| CN | 213911488 U | 8/2021 |
| KR | 20130022492 | 3/2013 |
| KR | 20130090961 | 8/2013 |
| KR | 101384565 | 4/2014 |
| KR | 20150115422 | 10/2015 |
| KR | 20190061183 | 6/2019 |
| KR | 10-2020-0115846 | 10/2020 |
| WO | 2011152891 A2 | 12/2011 |

* cited by examiner

STERILIZATION APPARATUS USING PLASMA AND ULTRAVIOLET LIGHT AND STERILIZATION SYSTEM COMPRISING THE SAME

TECHNICAL FIELD

Embodiments relate to a sterilization apparatus and a sterilization system for an airport including the same. More particularly, the embodiments relate to a sterilization apparatus that may sterilize baggage using plasma and ultraviolet light.

BACKGROUND ART

At an airport, the baggage of passengers must be checked through baggage scanners. The baggage is placed in baskets for the security check of the baggage through the baggage scanners. Since unhygienic items, such as shoes, may be placed in the baskets, and personal belongings of many people may be continuously placed in the baskets, the baskets are likely to be contaminated and may be exposed to various bacterial infections. In addition, passengers may indirectly contact each other when using the baggage scanners, and such indirect contacts may cause the transmission of various diseases. In particular, at times of strong contagious diseases spreading, such transmission issues may become more serious. To prevent the issues described above, a method of sterilizing baskets used at baggage scanners is in consideration.

Meanwhile, according to the procedure, the baggage is checked through baggage scanners after the passengers are identified and before the passengers go through immigration. Such baggage checkpoints are frequently crowded with passengers. In this circumstance, there are many spatial limitations in installing sterilization apparatuses for sterilizing the baggage. Therefore, there is a need for a method of flexibly disposing the sterilization apparatuses in structures around the baggage scanners at the airport.

In addition, there is a demand for a sterilization apparatus and sterilization system that does not take up so much space, while sterilizing the baggage in real time. In this regard, a cart auto-sterilizer is disclosed in Korean Registered Utility Model Publication No. 20-0427008. The invention of the cart auto-sterilizer is a device for sterilizing a cart, wherein the device is manufactured to fit the size of a cart and operates to be opened and closed by a detection sensor.

The above description has been possessed or acquired by the inventor(s) in the course of conceiving the present invention and is not necessarily an art publicly known before the present application is filed.

DISCLOSURE OF INVENTION

Technical Goals

An aspect provides a sterilization apparatus that may sterilize an object concurrently using a sterilizer radiating plasma rays and a sterilizer radiating ultraviolet light.

An aspect provides a sterilization system that may be installed near a baggage scanner or on a baggage scanner through the assembly of a sterilization apparatus according to a situation.

An aspect provides a sterilization apparatus that may control an operation of the sterilization apparatus depending on whether an object is brought into or brought out of the sterilization apparatus.

Technical Solutions

According to an aspect, there is provided a sterilization apparatus including a housing forming a sterilization space, a first sterilizer configured to radiate plasma rays toward the sterilization space, a second sterilizer configured to radiate ultraviolet light toward the sterilization space, a sensing unit configured to sense whether an object is placed in the sterilization space, and a controller configured to control an operation of the second sterilizer based on information sensed by the sensing unit.

The controller may be configured to, while the plasma ray is radiated toward the sterilization space, operate the second sterilizer to radiate the ultraviolet light toward the object in response to sensing that the object is brought into the sterilization space.

The controller may be configured to stop the operation of the second sterilizer not to radiate the ultraviolet light, in response to sensing that the object is brought out of the sterilization space.

The housing may include an entrance through which the object is brought into the sterilization space, and an exit through which the object is brought out of the sterilization space, and the object may be supported and conveyed by a conveyor belt disposed along a path passing through the sterilization space.

The sterilization apparatus may further include a cover member provided in the housing to cover the entrance and the exit, and configured to block exposure of the plasma ray and the ultraviolet light to the outside of the sterilization space.

The cover member may be configured to operate to open the entrance and the exit when the object passes through the entrance and the exit.

The second sterilizer may include a light emitting member disposed on a side of the sterilization space to emit the ultraviolet light, and a support member provided in the housing to cover the light emitting member, the support member including at least one perforation penetrating through a surface thereof to allow the ultraviolet light to pass therethrough.

The support member may include a polycarbonate material to ensure the heat resistance to the ultraviolet light.

The perforation may include a horizontal slit and a vertical slit, when viewed in a direction in which the ultraviolet light is radiated.

According to an aspect, there is provided a sterilization system for an airport, the sterilization system including a baggage scanner configured to scan the inside of an object through X-rays, a conveyor belt configured to convey the object along a path passing through the baggage scanner, and a sterilization apparatus comprising a sterilization space through which the object is to pass, a first sterilizer configured to radiate plasma rays toward the sterilization space, and a second sterilizer configured to radiate ultraviolet light toward the sterilization space.

The sterilization system may further include a connector connected to an entrance or an exit of a scanning space in the baggage scanner where the object is scanned, wherein the connector may be configured to connect the baggage scanner and the sterilization apparatus.

The sterilization apparatus may further include a sensing unit configured to sense whether the object is placed in the sterilization space, and if the sensing unit senses that the object is placed in the sterilization space, a controller configured to operate the second sterilizer to radiate the ultraviolet light.

Effects

According to embodiments, a sterilization apparatus may sterilize a basket and prevent contagious diseases through double sterilizations using a plurality of sterilizers.

According to embodiments, a sterilization apparatus may have mobility and thus, be flexibly and conveniently installed near a baggage scanner.

According to embodiments, a sterilization apparatus may reduce the loss of power occurring while in use.

BEST MODE FOR CARRYING OUT THE INVENTION

Figure 1:
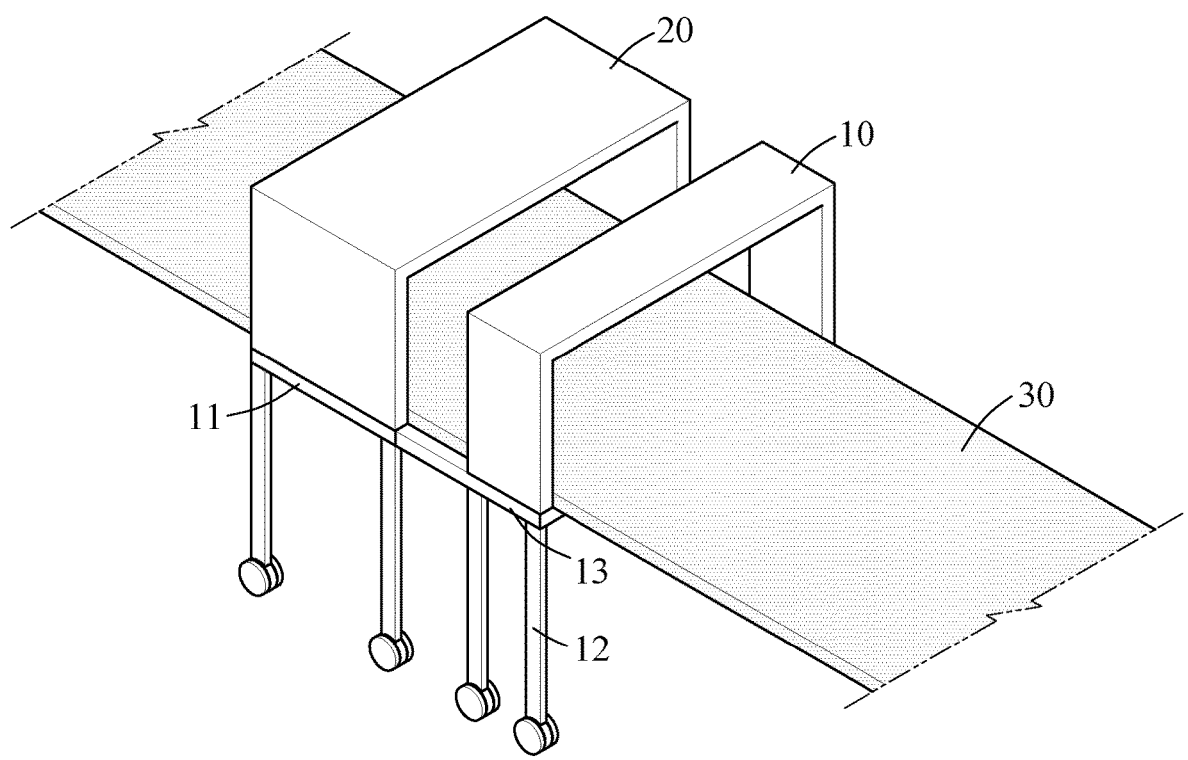
FIG. 1 is a schematic diagram illustrating a sterilization system for an airport according to an embodiment.

Hereinafter, embodiments of the present disclosure will be described with reference to the accompanying drawings. Regarding the reference numerals assigned to the components in the drawings, it should be noted that the same components will be designated by the same reference numerals, wherever possible, even though they are shown in different drawings. Also, in the description of the embodiments, detailed description of well-known related structures or functions will be omitted when it is deemed that such description will cause ambiguous interpretation of the present disclosure.

Also, in the description of the components, terms such as first, second, A, B, (a), (b) or the like may be used herein when describing components of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 2:
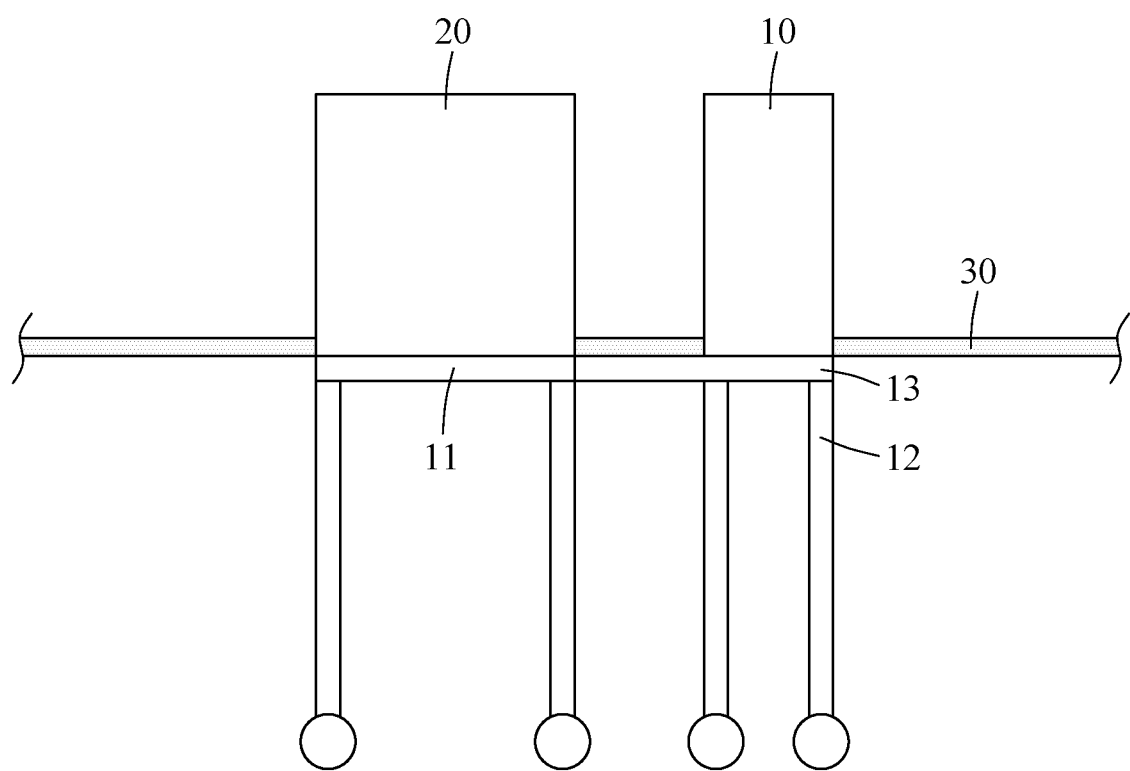
FIG. 2 is a side view illustrating a sterilization system for an airport according to an embodiment.
Figure 3:
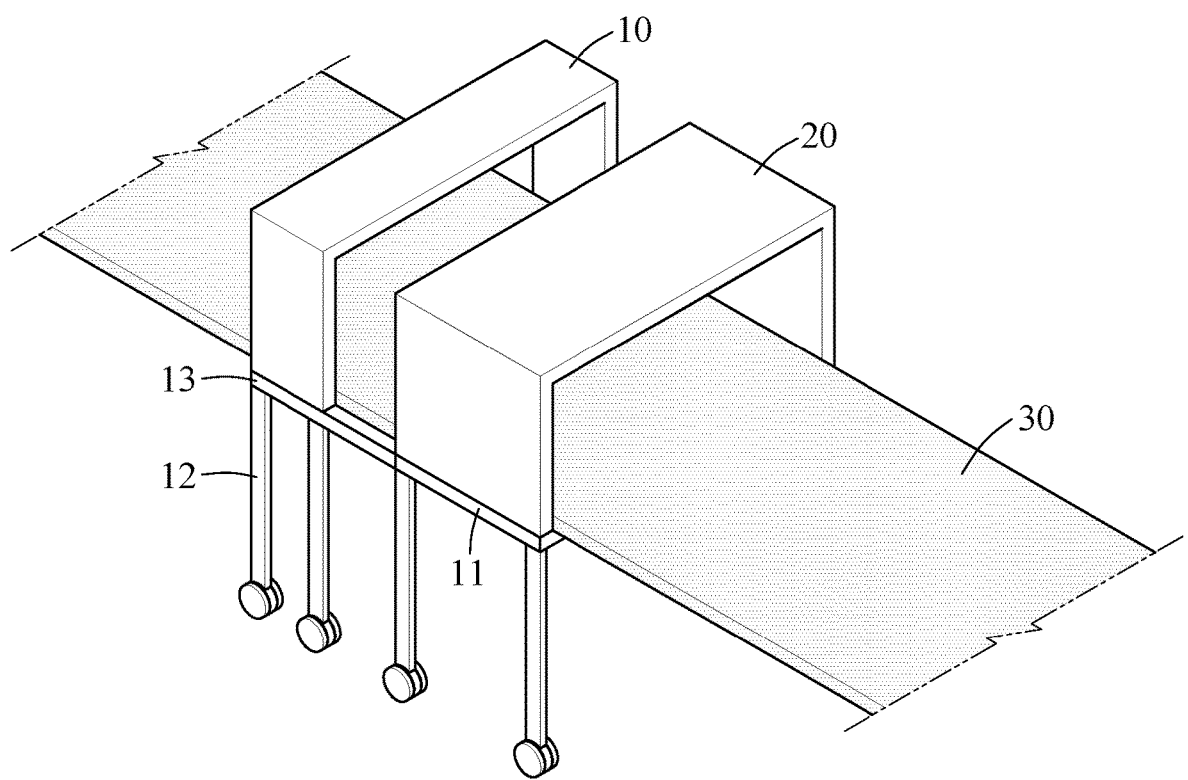
FIG. 3 is a schematic diagram illustrating a sterilization system for an airport according to an embodiment.
Figure 4:
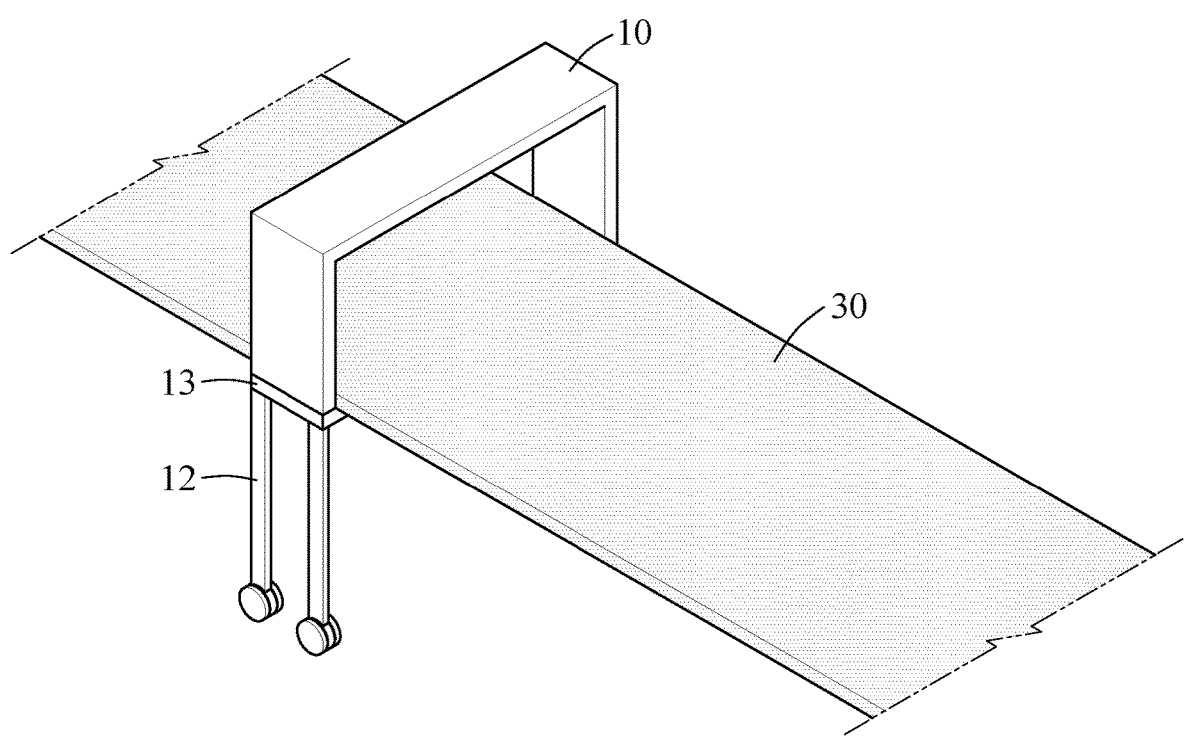
FIG. 4 is a schematic diagram illustrating a sterilization system for an airport according to an embodiment.

FIG. 1 is a schematic diagram illustrating a sterilization system for an airport, FIG. 2 is a side view illustrating the sterilization system for an airport according to an embodiment, FIG. 3 is a schematic diagram illustrating the sterilization system for an airport according to an embodiment, and FIG. 4 is a schematic diagram illustrating the sterilization system for an airport according to an embodiment.

Referring to FIGS. 1 through 4, the sterilization system for an airport may be installed and used at an airport. When a baggage scanner scans the inside of an object, the sterilization system may sterilize the scanned object. The object may be an article on which security check is to be performed, and may include, for example, personal baggage to be scanned for security check, a basket in which the personal baggage is to be placed, and the like.

The sterilization system may sterilize the object scanned for security check, or may sterilize the object irrespective of security check. The sterilization system may include a sterilization apparatus 10, a connector 11, a moving part 12, and a support part 13. The object may move from a baggage scanner 20 to the sterilization system through a conveyor belt 30.

The baggage scanner 20 may scan the inside of the object through X-rays. For example, according to the procedure at the airport, the inside of the baggage of a passenger must be checked. The baggage of the passenger is placed in a basket moving along the conveyor belt 30 and passes through the baggage scanner 20. When the object is placed in the baggage scanner 20, the baggage scanner 20 may inspect articles in the object through X-rays to determine whether the object contains any harmful items, prohibited items, or illegal items. The baggage scanner 20 may include a scanning space with an entrance and an exit, and the connector 11 connected to the entrance or the exit, such that the object may be scanned.

The conveyor belt 30 may move the object to the baggage scanner 20 along a path passing through the baggage scanner 20. The conveyor belt 30 may convey the object along the path passing through the baggage scanner 20, while supporting the object. The conveyor belt 30 may be provided in a carousel structure. Therefore, the object placed on the conveyor belt 30 continuously moves along the moving path of the conveyor belt 30 and thus, passes through the scanning space of the baggage scanner 20.

The sterilization apparatus 10 may sterilize the object conveyed through the conveyor belt 30. The sterilization apparatus 10 may allow the conveyor belt 30 to pass through the inner space thereof. For example, the sterilization apparatus 10 includes a sterilization space where the object is sterilized as described below, and the conveyor belt 30 may move the object along the path passing through the sterilization space.

The position of the sterilization apparatus 10 relative to the conveyor belt 30 may be varied. For example, the moving part 12 and the support part 13 may be connected to the sterilization apparatus 10 to adjust the position of the sterilization apparatus 10 relative to the conveyor belt 30.

The moving part 12 may be connected to the bottom of the sterilization apparatus 10 to support the sterilization apparatus 10. The moving part 12 may include a wheel at the lower end thereof to be in contact with the ground, thereby moving the sterilization apparatus 10. The conveyor belt 30 passes through the sterilization space of the sterilization apparatus 10. Thus, when the sterilization apparatus 10 is moved by means of the moving part 12, the position of the sterilization apparatus 10 may be changed on the path of the conveyor belt 30.

The support part 13 may fix the position of the sterilization apparatus 10 relative to the conveyor belt 30. For example, the support part 13 may be connected to the bottom of the sterilization space of the sterilization apparatus 10, and the conveyor belt 30 may be provided on the top of the support part 13. The support part 13 may connect the conveyor belt 30 and the sterilization apparatus 10, thereby maintaining the position of the sterilization apparatus 10 relative to the conveyor belt 30. A wheel may be provided at the lower end of the support part 13, and the sterilization apparatus 10 may be moved by means of the moving part 12.

However, the configuration of the moving part 12 and the support part 13 is provided as an example only, and various configurations for connecting the sterilization apparatus 10 and the conveyor belt 30 may be applicable to the sterilization system.

The connector 11 may connect the baggage scanner 20 and the sterilization apparatus 10. For example, the connector 11 may be connected to at least one of the front side or the rear side of the baggage scanner 20 provided on the path of the conveyor belt 30. In other words, the connector 11 may be connected to the entrance or exit portion of the scanning space of the baggage scanner 20 where the object is scanned.

The connector 11 may be connected to the sterilization apparatus 10. For example, as shown in FIG. 2, the connector 11 may be connected to the support part 13 of the sterilization apparatus 10. The connector 11 may be provided in a structure that may be assembled with the sterilization apparatus 10, thereby easily connecting the sterilization apparatus 10 to the baggage scanner 20. For example, the connector 11 may include a groove corresponding to the shape of the support part 13, such that the support part 13 of the sterilization apparatus 10 may fit therein. Therefore, at the airport, it is possible to selectively assemble and connect the connector 11 and the sterilization apparatus 10, as spatially necessary.

Depending on the position of the connector 11, the sterilization apparatus 10 may be connected to the front side or the rear side of the baggage scanner 20. By the above structure, the object conveyed by the conveyor belt 30 may pass through the sterilization apparatus 10 and the baggage scanner 20 in succession. For example, as shown in FIG. 1, the sterilization apparatus 10 may be connected to the rear side of the baggage scanner 20, that is, the rear portion of the scanning space. In this example, even if the object is contaminated during the security check, the object may be immediately sterilized through the sterilization apparatus 10, and thus the inspection of the baggage may be performed with improved hygiene.

As another example, if the sterilization apparatus 10 is connected to the front side of the baggage scanner 20, that is, the front portion of the scanning space, as shown in FIG. 3, the object may pass through the baggage scanner 20 immediately after sterilized by the sterilization apparatus 10. Thus, the sterilization system may prevent the scanning space of the baggage scanner 20 from being contaminated by the object.

However, the sterilization apparatus 10 may not be necessarily connected directly to the baggage scanner 20 as described above. Since the sterilization apparatus 10 is movable along the conveyor belt 12, the sterilization apparatus 10 may be installed separately at a predetermined position on the conveyor belt 30 as shown in FIG. 4. Therefore, according to the characteristics of a location where the sterilization system is installed, the position of the sterilization apparatus 10 may be appropriately adjusted.

The sterilization apparatus 10 may sterilize the object that is moved along the conveyor belt 30.

Figure 5:
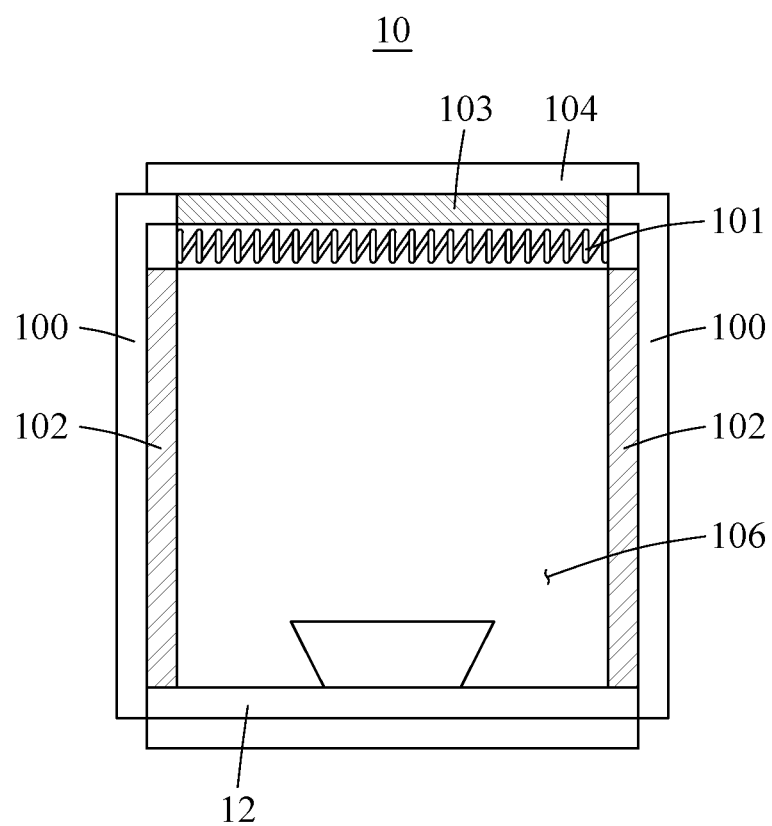
FIG. 5 is a front view illustrating a sterilization apparatus according to an embodiment.
Figure 6:
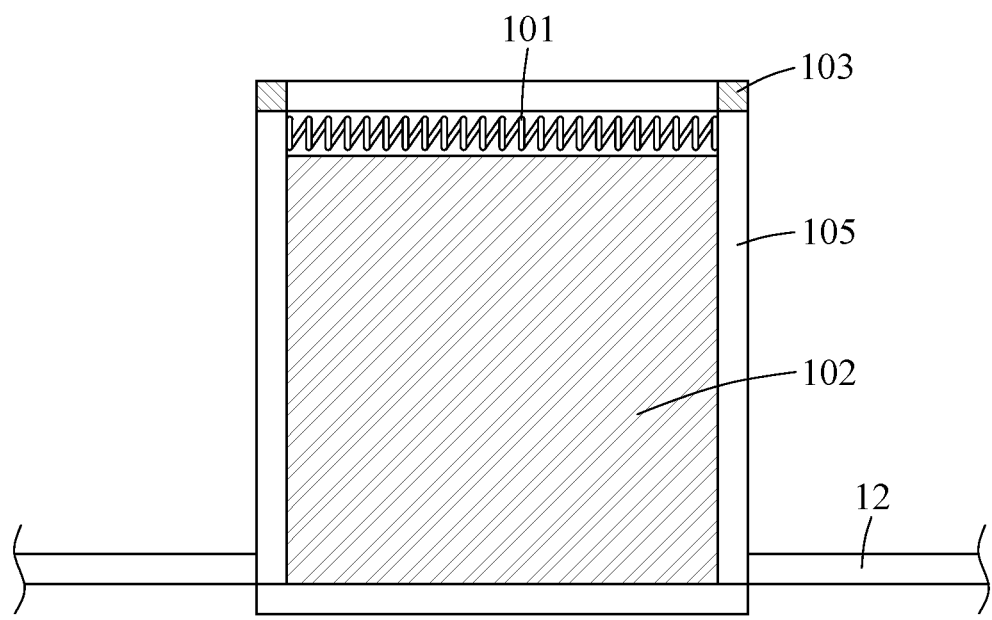
FIG. 6 is a side view illustrating a sterilization apparatus according to an embodiment.
Figure 7:
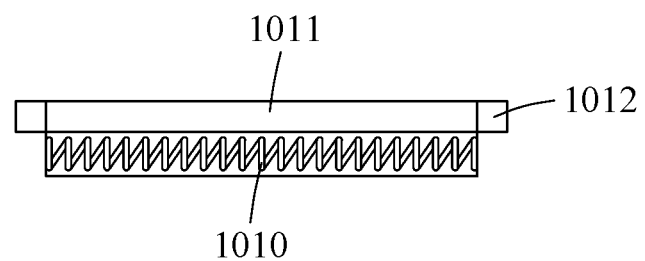
FIG. 7 is a schematic diagram illustrating a first sterilizer according to an embodiment.
Figure 8:
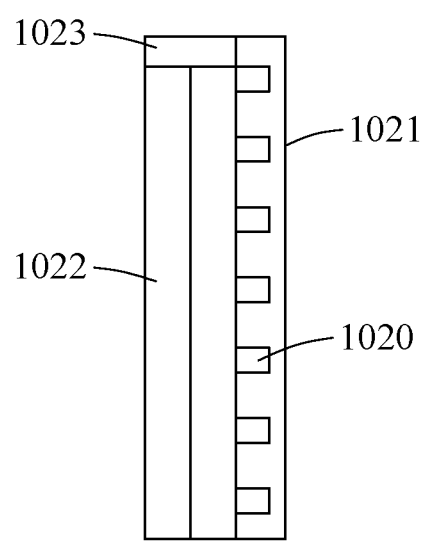
FIG. 8 is a schematic diagram illustrating a second sterilizer according to an embodiment.
Figure 9:
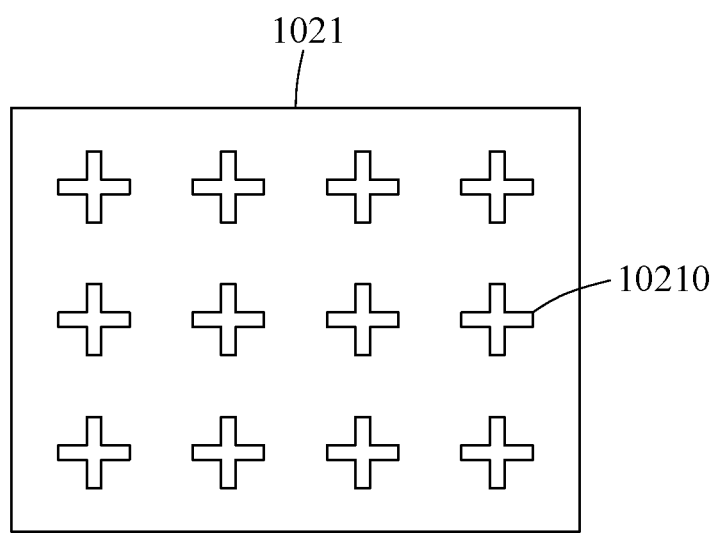
FIG. 9 is a front view illustrating a support member according to an embodiment.

FIG. 5 is a front view illustrating a sterilization apparatus according to an embodiment, FIG. 6 is a side view illustrating the sterilization apparatus according to an embodiment, FIG. 7 is a schematic diagram illustrating a first sterilizer according to an embodiment, FIG. 8 is a schematic diagram illustrating a second sterilizer according to an embodiment, and FIG. 9 is a front view illustrating a support member according to an embodiment.

Referring to FIGS. 5 through 9, the sterilization apparatus 10 may sterilize an object through two types of sterilization methods. For example, the sterilization apparatus 10 may sterilize the object through plasma rays and ultraviolet light. The sterilization apparatus 10 may include a housing 100, a first sterilizer 101, a second sterilizer 102, a sensing unit 103, a controller 104, and a cover member 105.

The housing 100 may form an exterior of the sterilization apparatus 10. The housing 100 may include a sterilization space 106 provided therein, where the object is to be sterilized, an entrance through which the object is brought into the sterilization space 106, and an exit through which the object is brought out of the sterilization space.

The conveyor belt 30 may be placed in the sterilization space 106. In other words, the conveyor belt 30 may be disposed along the path passing through the sterilization space 106, and move the object while supporting the object such that the object may pass through the sterilization space 106.

The first sterilizer 101 may radiate plasma rays toward the sterilization space 106. When the object is placed in the sterilization space 106, the object may be sterilized by the plasma ray radiated by the first sterilizer 101. Plasma may ionize air to generate vaporized hydrogen peroxide ($H_2O_2$). The vaporized hydrogen peroxide generated by plasma reacts with hydrogen ions ($H^+$) present in the cell membranes of microorganisms and destroys the cell membranes of the microorganisms. Thus, the vaporized hydrogen peroxide may have a high sterilization performance Plasma sterilization may be performed at a low temperature of 50° C. or less and thus, has an advantage of easily sterilizing articles vulnerable to heat.

The first sterilizer 101 may be provided on the upper portion of the housing 100, that is, the upper portion of the sterilization space 106. The first sterilizer 101 may continuously radiate plasma rays toward the sterilization space 106. That is, regardless of whether the object is placed in the sterilization space 106, the first sterilizer 101 may radiate plasma toward the sterilization space 106. Since the conveyor belt 30 continuously moves along the path passing through the sterilization space 106, a portion of the conveyor belt 30 placed in the sterilization space 106 may be sterilized by the plasma ray radiated by the first sterilizer 101. The first sterilizer 101 may include a plasma generating member 1010, and a first fixing member 1011.

The plasma generating member 1010 may generate plasma. The plasma generating member 1010 may generate plasma through the direct current (DC) discharge principle. For example, the plasma generating member 1010 may include a pair of plates to which a positive electrode and a negative electrode are respectively applied, and generate plasma by causing discharging with a voltage applied between the pair of plates.

The first fixing member 1011 may connect the plasma generating member 1010 to the housing 100. For example, the first fixing member 1011 may fix the plasma generating member 1010 to the top surface of the sterilization space 106. The first fixing member 1011 may set the direction in which the plasma generated by the plasma generating member 1010 is radiated, to a direction toward the center of the sterilization space 106. Since the plasma generating member 1010 generates plasma at the upper portion of the sterilization space 106 by means of the first fixing member 1011, hydrogen peroxide gas generated by the plasma may be radiated toward the lower portion of the sterilization space 106. Therefore, the first sterilizer 101 may sterilize the air in the sterilization space 106, the conveyor belt 30 placed at the lower side thereof, and the object placed on the conveyor belt 30.

The second sterilizer 102 may radiate ultraviolet light toward the sterilization space 106. When the object is placed in the sterilization space 106, the object may be sterilized by the ultraviolet light radiated by the second sterilizer 102. The second sterilizer 102 may be disposed on the front side of the sterilization apparatus 10, that is, on both sides of the sterilization space 106 based on the direction in which the conveyor belt 30 moves. The second sterilizer 102 may include a light emitting member 1020, a support member 1021, and a second fixing member 1022.

The light emitting member 1020 may generate ultraviolet light. The light emitting member 1020 may include, for example, a light emitting diode (LED) that generates ultraviolet light. For example, the light emitting member 1020 may radiate the ultraviolet light as a short-wavelength ultraviolet (UV-C) ray. The short-wavelength ultraviolet light has a short wavelength and thus, may sterilize bacteria, mold, and microorganisms present in the object or the air. The short-wavelength ultraviolet light may change the DNA of bacteria, mold, and microorganisms and destroy their nuclei, and ultimately destroy the cells such as the bacteria and the mold.

During the security check, the baggage of many passengers indirectly contacts each other and thus, may transmit bacteria or microorganisms. The second sterilizer 102 may eradicate bacteria and microorganisms on the baggage placed in the sterilization space through ultraviolet sterilization.

The support member 1021 may be provided in the housing 100 to cover the light emitting diode. The support member 1021 may be provided in the sterilization space 106 to cover the light emitting member 1020. Since the support member 1021 covers the light emitting member 1020, it is possible to prevent the light emitting member 1020 from being damaged by an impact occurring while the object is moved relative to the sterilization space 106. The support member 1021 may include a material that has heat resistance to ultraviolet lights and impact resistances to impact from the outside. For example, the support member 1021 may include polycarbonate. If the support member 1021 includes polycarbonate, it is possible to secure impact resistance enough to prevent the light emitting diode from being damaged due to impacts resulting from contact with the object, and it is possible to prevent the melting phenomenon caused by heat of the light emitting diode.

The support member 1021 may include at least one perforation penetrating through a surface thereof to allow the ultraviolet light from the light emitting member 1020 to be radiated toward the sterilization space. The ultraviolet light generated by the light emitting diode may pass through the support member 1021 via the perforation and be radiated to the sterilization space 106. In this example, the ultraviolet light may spread over a wide radius as being diffracted while passing through the perforation. The perforation may be provided in the form of a slit with a width smaller than a length so that the ultraviolet light may be easily diffracted. For example, as shown in FIG. 9, based on the direction in which the ultraviolet light is radiated, the perforation may be provided in the form including a horizontal slit and a vertical slit, for example, in the form of a cross 10210. Light spreads in the width direction of a slit while being diffracted. Thus, if the perforation includes a horizontal slit and a vertical slit, light may be diffracted in horizontal and vertical directions at the same time.

The second fixing member 1022 may fix the light emitting member 1020 and the support member 1021 to the housing 100. The light emitting member 1020 and the support member 1021 may be fixed to the side of the sterilization space 106 by means of the second fixing member 1022.

The first sterilizer 101 and the second sterilizer 102 may be assembled with each other. For example, the first sterilizer 101 and the second sterilizer 102 may include a first connecting member 1012 and a second connecting member 1023 that are connected to each other. Through the connection of the first connecting member 1012 and the second connecting member 1023, the first sterilizer 101 and the second sterilizer 102 may be configured as a single assembly.

The sensing unit 103 may sense whether an object is placed in the sterilization space 106. The sensing unit 103 may detect whether the object is brought in the sterilization space 106 and whether the object is brought out of the sterilization space 106. For example, the sensing unit 103 may include infrared sensors installed at the entrance and the exit of the housing 100. The infrared sensors may recognize optical information reflected after an infrared ray is radiated toward the conveyor belt, thereby sense whether the object is placed on the conveyor belt 30.

The controller 104 may control the operation of the second sterilizer 102 based on the information sensed by the sensing unit 103. For example, in response to sensing that the object is brought in the sterilization space 106, the controller 104 may operate the second sterilizer 102 to radiate ultraviolet light toward the sterilization space 106, that is, to radiate ultraviolet light toward the object placed in the sterilization space 106. In detail, if the sensing unit 12 does not recognize that the object is brought out after recognizing that the object is brought in, the controller 104 may determine that the object is in the sterilization space by receiving in-out information of the object from the sensing unit 103. In response to recognizing the presence information of the object, the controller 104 may control the light emitting member 1020 of the second sterilizer 102 to radiate ultraviolet light.

In response to sensing that the object is brought out of the sterilization space 106, the controller 104 may stop the operation of the second sterilizer 102 not to radiate ultraviolet light. In detail, if the sensing unit 12 recognizes that the object is brought in once and then recognizes that the object is brought out once, the controller 104 may determine that the object is not in the sterilization space 106. The controller 104 may stop the ultraviolet emission of the light emitting member 1020 of the second sterilizer 102 after determining that the object is not present in the sterilization space 106.

In summary, the first sterilizer may continuously perform plasma sterilization regardless of whether or not an object is present in the sterilization space 106, whereas the second sterilizer 102 may perform sterilization only when the object is present in the sterilization space 106. The plasma sterilization of the first sterilizer 101 is an indirect sterilization method through the generated hydrogen peroxide and thus, has a continuous sterilization effect for a large space, while the ultraviolet sterilization of the second sterilizer 102 is a direct sterilization method through contact with ultraviolet lights and thus, has a short-term sterilization effect for a narrow space. Therefore, the ultraviolet sterilization through the second sterilizer 102 may have optimal sterilization efficiency while the object is placed in the sterilization space 106. Accordingly, if the second sterilizer unit 102 selectively radiates ultraviolet light depending on whether the object is placed in the sterilization space 106, sterilization may be performed more efficiently, whereby unnecessary power consumption may be prevented.

The cover member 105 may prevent the plasma and ultraviolet lights from being exposed from the sterilization space 106. Accordingly, it is possible to prevent a person present outside of the sterilization apparatus 10 from being exposed to the plasma or ultraviolet light.

The cover member 105 may be provided in the housing 100 to cover the entrance and the exit. The cover member 105 may operate to open the entrance and the exit only when the object passes through the entrance and the exit. For example, the cover member 105 may be selectively opened and closed according to a control signal, and the controller 104 may control the operation of opening and closing the cover member 105 based on information sensed by the sensing unit 103. In detail, when the sensing unit 103 provided at the entrance recognizes an object moved to the front of the sterilization apparatus 10, the cover member 105 provided at the entrance may be opened. Further, when the sensing unit 103 provided at the exit recognizes an object to be moved out of the sterilization space 106 after sterilization, the cover member 105 provided at the exit may be opened.

In another example, the cover member 105 may require no manipulation by a person to cover the entrance and the exit without restricting the movement of the object on the conveyor belt 30. That is, the object may be brought in and out without a special device. For example, when curtains are provided at the entrance and the exit, an object may be brought in and out of the sterilization space regardless of control by a person, and the plasma and ultraviolet lights may be blocked not to be exposed to the outside.

Consequently, the sterilization apparatus 10 may secure more effective sterilization efficiency by sterilizing the object through the first sterilizer 101 that performs plasma sterilization and the second sterilizer 102 that performs ultraviolet sterilization. Further, the operation of the second sterilizer 102 is selectively performed by recognizing whether an object is present in the sterilization space 106, whereby unnecessary power consumption may be prevented. In particular, the first sterilizer 101 and the second sterilizer 102 may be provided in a structure to be assembled, whereby the sterilization apparatus 10 may be assembled and provided in various forms, as spatially necessary.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

The invention claimed is:

1. A sterilization apparatus, comprising:
a housing forming a sterilization space;
a first sterilizer configured to radiate plasma rays toward the sterilization space;
a second sterilizer configured to radiate ultraviolet light toward the sterilization space;
a sensing unit configured to sense whether an object is placed in the sterilization space; and
a controller configured to control an operation of the second sterilizer based on information sensed by the sensing unit;
wherein the controller is configured to,
while the plasma ray is radiated toward the sterilization space,
operate the second sterilizer to radiate the ultraviolet light toward the object in response to sensing that the object is brought into the sterilization space.

2. The sterilization apparatus of claim 1, wherein the controller is configured to stop the operation of the second sterilizer not to radiate the ultraviolet light, in response to sensing that the object is brought out of the sterilization space.

3. The sterilization apparatus of claim 1, wherein the housing comprises an entrance through which the object is brought into the sterilization space, and an exit through which the object is brought out of the sterilization space, and
the object is supported and conveyed by a conveyor belt disposed along a path passing through the sterilization space.

4. The sterilization apparatus of claim 3, further comprising:
a cover member provided in the housing to cover the entrance and the exit, and configured to block exposure of the plasma ray and the ultraviolet light to the outside of the sterilization space.

5. The sterilization apparatus of claim 4, wherein the cover member is configured to operate to open the entrance and the exit when the object passes through the entrance and the exit.

6. A sterilization apparatus, comprising:
a housing forming a sterilization space;
a first sterilizer configured to radiate plasma rays toward the sterilization space;
a second sterilizer configured to radiate ultraviolet light toward the sterilization space;
a sensing unit configured to sense whether an object is placed in the sterilization space; and
a controller configured to control an operation of the second sterilizer based on information sensed by the sensing unit,
wherein the second sterilizer comprises:
a light emitting member disposed on a side of the sterilization space to emit the ultraviolet light; and
a support member provided in the housing to cover the light emitting member, the support member including at least one perforation penetrating through a surface thereof to allow the ultraviolet light to pass therethrough, and
wherein the support member includes a polycarbonate material to ensure the heat resistance to the ultraviolet light.

7. The sterilization apparatus of claim 6, wherein the perforation includes a horizontal slit and a vertical slit, when viewed in a direction in which the ultraviolet light is radiated.

* * * * *